United States Patent [19]

Martin et al.

[11] 4,187,297
[45] Feb. 5, 1980

[54] 3-DE-O-METHYL-2-N-ACYL AND ALKYL FORTIMICINS A AND B

[75] Inventors: Jerry R. Martin; John S. Tadanier, both of Waukegan; Paulette Collum, Zion, all of Ill.

[73] Assignee: Abbott Laboratories, North Chicago, Ill.

[21] Appl. No.: 863,014

[22] Filed: Dec. 21, 1977

[51] Int. Cl.² ............... A61K 31/71; C07H 15/22
[52] U.S. Cl. .................. 424/180; 536/17 R; 424/181
[58] Field of Search .................. 424/180; 536/17

[56] References Cited

U.S. PATENT DOCUMENTS

| 3,931,400 | 1/1976 | Nara et al. | 424/118 |
| 3,976,768 | 8/1976 | Nara et al. | 424/118 |

Primary Examiner—Johnnie R. Brown
Attorney, Agent, or Firm—Robert L. Niblack; Gildo E. Fato; Joyce R. Niblack

[57] ABSTRACT

3-De-O-methyl-2'-N-acyl and alkyl fortimicin B derivatives represented by the formula

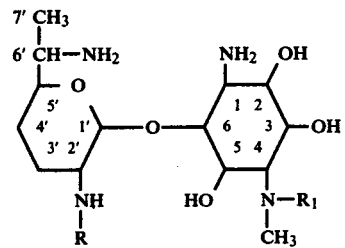

wherein R is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, an amino acid residue, hydroxyacyl, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, hydrogen; the pharmaceutically acceptable salts thereof; pharmaceutical compositions containing the compounds; and methods of making and using the compounds. The compounds are antibiotics.

10 Claims, No Drawings

3-DE-O-METHYL-2-N-ACYL AND ALKYL FORTIMICINS A AND B

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide structures which are less toxic than the parent antibiotic. Further, in the same family series mentioned above, certain modifications alter the antibacterial spectrum advantageously either by increasing the intrinsic activity or increasing activity against resistant strains.

Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic.

The present invention provides new and useful fortimicin derivatives.

SUMMARY OF THE DISCLOSURE

3-De-O-methyl-2'-N-acyl and alkyl fortimicin B and fortimicin B derivatives, 3-de-O-methyl-4,2'-di-N-acyl and dialkyl fortimicin B derivatives, 3-de-O-methyl-4-N-acyl-2'-N-alkyl and 3-de-O-methyl-4-N-alkyl-2'-N-acyl-3-de-O-methyl forticimin B derivatives are provided by this invention as well as their salts, intermediates, processes for making the compounds, and compositions and methods employing the compounds.

The fortimicin derivatives of this invention are antibiotics which are effective against various Gram-negative and Gram-positive bacteria and can be administered orally or parenterally in daily dosages of from about 1 to about 100 mg/kg of body weight daily to mammalian patients showing symptoms of infection caused by one of the susceptible bacteria.

The compounds can also be used as preservatives for various industrial solutions, in antibacterial scrub solutions for cleaning laboratory bench tops and the like. They are also useful as intermediates in preparing other fortimicin derivatives which have anti-bacterial activity.

The base compounds of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The present invention provides 3-de-O-methyl-2'-N-acyl and alkyl fortimicin B derivatives represented by Formula I:

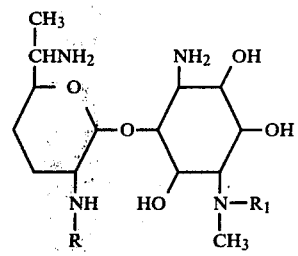

wherein R is acyl, aminoacyl, N-monoloweralkylaminoacyl, hydroxyacyl N,N-diloweralkylaminoacyl, hydroxy-substituted aminoacyl, an amino acid residue, loweralkyl, aminoloweralkyl, hydroxyloweralkyl, aminohydroxyloweralkyl, N-loweralkylaminoloweralkyl, N,N-diloweraminoalkyl loweralkyl, N-loweralkylaminohydroxyloweralkyl N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen; and the pharmaceutically acceptable salts thereof.

The term "pharmaceutically acceptable salts" refers to non-toxic acid addition salts of the bases which are generally prepared by reacting the base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula

wherein $R_1$ is loweralkyl, i.e., acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "amino acid residue" refers to D, L or DL amino acid residues and includes but is not limited to glycyl, alanyl, sarcosyl, tyrosyl, phenylalanyl, methionyl, seryl, lysyl, asparaginyl, isoleucyl, leucyl, threonyl, valyl, prolyl, glutaminyl, tryptophanyl glutamyl and the like.

The 3-de-O-methyl-2'-N-acylfortimicin B derivatives can be prepared by rearrangement of the corresponding 3-de-O-methyl-4-N-substituted fortimicins B of Formula II

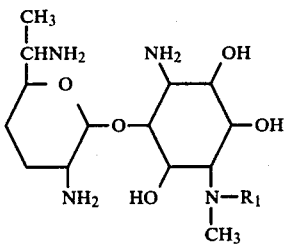

wherein R₁ is as defined in Formula I, or of 3-de-O-methyl fortimicin A, represented by Formula III

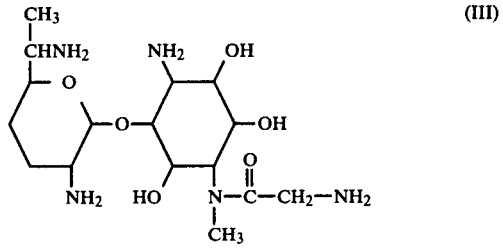 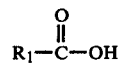

Fortimicin A and Fortimicin B are prepared according to the methods of U.S. Pat. Nos. 3,976,768 and 3,931,400. The preparation of representative 3-de-O-methyl-4-N-acyl fortimicin B derivatives is set forth in the Examples herein.

The 3-de-O-methyl intermediates of Formula II and III can be readily prepared by reacting fortimicin B, or a derivative thereof containing the fortimicin moiety with excess metallic lithium in an amine solvent such as ethylamine or ethylenediamine. The reactants are admixed in the solvent and the reaction allowed to proceed at a suitable temperature for the desired period. The resulting 3-de-O-methylfortimicin B, or other derivative, is isolated by conventional column chromatographic methods.

The 3-de-O-methylfortimicin B prepared above can be reacted with N-(benzyloxycarbonyloxy)succinimide to prepare 1, 2′,6′-tri-N-benzyloxycarbonyl-3-de-O-methylfortimicin B by methods well known in the art and set forth in the Examples herein. The product formed in the above reaction is isolated by column chromatography and 4-N-acylated by treatment with, for example an active carboxylic acid ester, i.e., a suitable N-benzyloxycarbonyl protected amino acid ester prepared by the method of M. Fujino et al., *Chem. Pharm-Bull.*, Japan, 22, p. 1857 (1974). The tribenzyloxycarbonyl-3-de-O-methyl-4-N-acylfortimicins prepared as above are conveniently reduced to the corresponding 4-N-alkyl derivatives with diborane. After isolation by column chromatography the benzyloxycarbonyl groups of both the 4-N-acyl and 4-N-alkyl derivatives are conveniently removed by catalytic hydrogenolysis and the products may be conveniently isolated as the free base or a salt.

The 3-de-O-methyl-2′-N-acetyl and 2′-N-glycyl fortimicins B are then readily prepared by rearrangement of corresponding 3-de-O-methyl 4-N-acyl-substituted fortimicins. In one method of preparation, the stable acid addition salts of the 3-de-O-methyl 4-N-substituted fortimicins are converted to the free bases by, for example, use of a suitable anion exchange resin. The 2′-N-substituted-3-de-O-methyl-fortimicins B are then prepared by placing the corresponding 4-N-substituted-3-de-O-methyl-fortimicin free bases in water solution which readily arranges the substituent at the nitrogen attached to C₄ to the nitrogen attached to C₂′. Treatment of the 2′-N-substituted-3-O-dimethyl fortimicins B with suitable N-acetylating agents such as N-(benzyloxycarbonyloxy)succinimide, benzyloxycarbonyl chloride or O-(benzyloxycarbonyl) p-nitrophenol in a solvent system such as N,N-dimethylformamide-methanol-water results in the 1,2′,6′-tri-N-protected intermediate, i.e., 1,2′,6′-tribenzyloxy intermediate which can then by acylated with a variety of activated carboxylic acid derivatives, such as a carboxylic acid and hydride, a carboxylic acid chloride, an active carboxylic acid ester, or a carboxylic acid azide.

The active esters may be conveniently prepared by reacting the appropriate carboxylic acid, $$R_1-\overset{O}{\underset{\|}{C}}-OH$$

with, for example, 1-hydroxybenzotriazole, N-hydroxysuccinimide, or N-hydroxy-5-norborene-2,3-dicarboximide according to the method of M. Fujino et al., *Chem Pharm. Bull,* Japan, 22, 1857 (1974) wherein R₁ is an acyl group as defined in Formula I.

After completion of the N-acylation of the C₄-N-methylamino group, it is necessary to remove the benzyloxycarbonyl protecting groups, most conveniently carried out by hydrogenolysis over a palladium on carbon catalyst. The fortimicin analogs thus prepared are conveniently isolated as the hydrochloride salts when the hydrogenolysis is carried out in the presence of a slight excess of hydrochloric acid.

The 3-de-O-methyl-2′-N-alkylfortimicins B are conveniently prepared by treatment of the corresponding 2′-N-acylfortimicins B with a suitable reducing agent such as diborane or a metal hydride such as lithium aluminum hydride. The resulting 2′-N-alkylfortimicins B derivative can then be treated with a suitable N-acylating agent as described above leaving the C₄-methylamino group free. C₄-N-acylation and deblocking as described previously gives the 3-de-O-methyl-4′-N-acyl-2-N-alkylfortimicin B.

The 3-de-O-methyl-2′-N-alkyl-4-N-alkylfortimicins B are conveniently prepared by treating the desired N-protected 3-de-O-methyl-2′-N-acylfortimicin B with a suitable reducing agent, e.g., diborane. Deblocking by hydrogenolysis as described above gives 3-de-O-methyl-4,2′-di-N-alkylfortimicins B. Alternatively, the 3-de-O-methyl-4,2′-di-N-alkylfortimicins can be prepared by reduction of a suitable 3-de-O-methyl-4-N-acyl-2′-N-alkylfortimicin B. For example, a 3-de-O-methyl-4-N-acyl-2′-N-alkylfortimicin B or an N-protected 3-de-O-methyl-4-N-acyl-2′-N-alkylfortimicin B may be treated with a suitable reducing agent, e.g., diborane. In the case of the resulting N-protected 3-de-O-methyl-4,2′-di-N-alkylfortimicin B, the N-blocking groups can be conveniently removed by hydrogenolysis providing the desired 3-de-O-methyl-4,2′-di-N-alkylfortimicin B.

Alternatively, the 3-de-O-methyl-2′-N-acyl derivatives of this invention can be prepared by reacting 3-de-O-methylfortimicin B with tert-butyl-S-(4,6-dimethylpyrimidin-2-yl) thiolcarbonate to obtain the 3-de-O-methyl-2′-tert-butyloxycarbonyl (Boc) fortimicin B intermediate.

The 2'-Boc-intermediate is then reacted with a suitable acylating agent, i.e., N(-benzyloxycarbonyl)succinimide which results in the 3-de-O-methyl-1,6'-di-N-benzyloxy-2'-Boc-fortimicin B intermediate. Treatment of the latter intermediate with an active ester of N-protected glycine, e.g., the N-hydroxysuccinimide ester of N-benzyloxycarbonylglycine in the presence of a suitable solvent system such as N,N-dimethylformamide-methanol-water results in 3-de-O-methyl-2'-Boc-tribenzyloxycarbonyl fortimicin A.

Deprotection of the 2'-amino group is effected by reacting the latter intermediate with, for example, $CF_3COOH$. 2'-Acylation or alkylation is then conveniently accomplished by reacting the latter 2'-deprotected intermediate with a suitable carboxylic acid ester as described above or with a suitable aldehyde ($R_1CHO$) in the presence of sodium borohydride. Deprotection is then completed by hydrogenolysis in the presence of 5% palladium on carbon catalyst which results in the desired 2'-acyl or 2-alkyl derivatives.

The following examples further illustrate the present invention.

EXAMPLE 1

3-De-O-methylfortimicin B

To a solution of 2.0 g. of fortimicin B free base in 50 ml. of freshly distilled ethylamine is added 40 ml. of ethylamine containing 0.859 g. of lithium wire freshly cut into small pieces. The dark blue reaction mixture is stirred under reflux for 2 hours, then methanol is slowly added to consume excess lithium. The solvents are removed under reduced pressure and the resulting organic products are separated from the lithium salts by column chromatography on silica gel prepared and eluted with the lower phase of a mixture of chloroform-methanol-concentrated ammonium hydroxide (1:1:1 v/v/v). Fractions enriched in 3-de-O-methylfortimicin B are collected and rechromatographed on a column of a cation exchange resin, carboxylic type, such as Bio Rex 70, 100–200 mesh, ($NH_4$ form) Elution with a gradient of water to 1 N $NH_4OH$ gave fractions containing pure 3-de-O-methylfortimicin B. Lyophilization gave 0.267 g. of colorless material: $[\alpha]_D^{24}+41.4°$ (c 1.02, $CH_3OH$); IR 3370, 1585 cm$^{-1}$; PMR ($D_2O$) 1.5 ($C_{6'}$-$CH_3$, $J_{6',7'}=6.5$ Hz), 2.83 ($C_4$-N-$CH_3$), 5.53 ($H_{1'}$, $J_{1',2'}=3.8$ Hz); Mass spec M+ 334.222 Calculated for $C_{14}H_{30}N_4O_5$ 334.2216.

EXAMPLE 2

1,2',6'-Tri-N-benzyloxycarbonyl-3-de-O-methylfortimicin B

To a stirring, ice-bath cooled solution of 3-de-O-methylfortimicin B free base (1.59 g) in 24 ml water and 48 ml methanol is added 3.55 g of N-(benzyloxycarbonyloxy)succinimide. The reaction is stirred at icebath temperature for 4 hours and then at room temperature for 22 hours. The reaction is concentrated under reduced pressure and poured into 400 ml. water to which is added 200 ml. chloroform. The organic layer is separated and washed with water and dried ($MgSO_4$). The chloroform is evaporated and the residue chromatographed on slica gel prepared and eluted with a solvent system consisting of chloroform-methanol-concentrated ammonium hydroxide (23.4:1.4:0.1 v/v/v) Fractions containing pure 1, 2', 6'-tri-N-benzyloxycarbonyl-3-de-O-methylfortimicin B are collected and evaporated to dryness to give 1.70 g. of product: $[\alpha]_D^{23}+19.4°$ (c 1.0, $CH_3OH$); IR 3437, 3350, 1705, 1505 cm$^{-1}$; PMR (CDCl$_3$) δ0.99 ($C_{6'}$-$CH_3$, $J_{6',7'}=5.0$ Hz), 2.27 ($C_4$-N-$CH_3$), 7.27 (Cbz).

Analysis: Calculated for $C_{33}H_{48}N_4O_{11}$: C, 61.94; H, 6.57; N, 7.60; Found: C, 61.83; H, 6.74; N, 7.51

EXAMPLE 3

Tetra-N-benzyloxycarbonyl-3-de-O-methylfortimicin A

To a stirred solution of 0.80 g. of 1, 2', 6'-tri-N-benzyloxycarbonyl-3-de-O-methylfortimicin B in 5.35 ml. of tetrahydrofuran is added 0.399 g of N-hydroxysuccinimidyl-N-benzyloxycarbonyl glycine. Stirring is continued for 22 hours at room temperature. The reaction is concentrated to dryness under reduced pressure and the resulting product chromatographed on a column of silica gel with a solvent system consisting of benzene-methanol-95% ethanol-concentrated ammonium hydroride (23.5:1.4:2.0:0.2 v/v/v/v). Fractions containing the desired product are taken to dryness to give 0.488 g. of tetra-N-benzyloxycarbonyl-3-de-O-methylfortimicin A as a colorless glass: $[\alpha]_D^{24}+45.2°$ (c1.03, $CH_3OH$); IR 3425, 1705, 1645, 1500 cm$^{-1}$; PMR (CDCl$_3$) δ1.15 ($C_{6'}$-$CH_3$), 2.9 ($C_4$-N-$CH_3$), 7.28 (Cbz).

Analysis: Calculated for $C_{48}H_{57}N_5O_{14}$: C, 62.13; H, 6.19; N, 7.55; Found: C, 61.80; H, 6.31; N, 7.64

EXAMPLE 4

Tetra-N-benzyloxycarbonyl-3-de-O-methylfortimicin A

To a stirred solution of 0.525 g. of 1, 2', 6'-tri-N-benzyloxycarbonyl-3-de-O-methylfortimicin B, 0.199 g. of N-benzyloxycarbonylglycine and 0.228 g. of 1-hydroxybenzotriazole monohydrate in 3.0 ml. tetrahydrofuran is added 0.88 g of N,N'-dicyclohexylcarbodiimide dissolved in 1.5 ml. tetrahydrofuran. An additional 1.5 ml. of tetrahydrofuran is used to rinse all the N,N'-dicyclohexylcarbodiimide into the reaction vessel. Stirring is continued for 22 hours at ambient temperature. Insoluble dicyclohexylurea is removed by filtration. The filtrate is concentrated to dryness under reduced pressure to yield a yellow froth. The froth is chromatographed on a column of silica gel using a solvent system consisting of benzene-methanol-95% ethanol-concentrated ammonium hydroxide (23.5:1.4:2.0:0.2 v/v/v/v). Fractions containing the majority of the product are taken to dryness and rechromatographed on a column of Sephadex LH20 prepared and eluted with 95% ethanol. Fractions containing pure product are collected and the solvent removed under reduced pressure to give 0.105 g.of tetra-N-benzyloxycarbonyl-3-de-O-methylfortimicin A identical in all respects with the same material prepared in Example 3.

EXAMPLE 5

Tetra-N-benzyloxycarbonyl-3-de-O-methyl-4-N-sarcosylfortimicin B

To a stirred solution of 0.298 g of 1,2',6'-tri-N-benzyloxycarbonyl-3-de-O-methylfortimicin B, 0.113 g. of N-benzyloxycarbonylsarcosine and 0.129 g. of 1-hydroxybenzotriazole in 3.0 ml. of tetrahydrofuran is added 0.107 g. of N,N'-dicyclohexylcarbodiimide in 1.5 ml. tetrahydrofuran. An additional 1.5 ml. of tetrahydrofuran is used to rinse all the N,N'-dicyclohexylcarbodiimide into the reaction flask. Stirring is continued for 16 hours at room temperature. Insoluble dicyclohexylurea is removed by filtration and the filtrate concentrated to yield a pale yellow solid. The solid is chromatographed on a column of silica gel using a solvent system consisting of benzene-methanol-95% ethanol-concentrated ammonium hydroxide (23.5;1.4;2.0; 0.2 v/v/v/v). Fractions containing homogeneous material are taken to dryness. Other fractions containing a minor second component are rechromatographed on a column of silica gel using a solvent system consisting of benzene-methanol-concentrated ammonium hydroxide (85:15:1 v/v/v). Homogeneous fractions are combined with material obtained in the first column to give 0.709 g. of tetra-N-benzyloxycarbonyl-3-de-O-methyl-4-N-sarcosylfortimicin B as a glass: $[\alpha]_D^{24} + 42.9°$ (c 1.01, $CH_3OH$); IR 3435, 1703, 1635, 1500 $cm^{-1}$; PMR ($CDCl_3$) δ 1.17 ($C_6'$-$CH_3$), ~2.9 (broad) (Sarcosyl-N-$CH_3$), 2.99 ($C_4$-N-$CH_3$), 4.83 ($H_{1'}$, $J_{1',2'}=3.5$), 7.31 (Cbz).

Analysis: Calculated for $C_{49}H_{59}N_5O_{14}$: C, 62.48; H, 6.31; N, 7.43; Found: C, 62.35; H, 6.65; N, 7.57

EXAMPLE 6

3-De-O-methylfortimicin A tetrahydrochloride

Tetra-N-benzyloxycarbonyl-3-de-O-methylfortimicin A (0.14 g.) in 25 ml. 0.2 N hydrochloric acid in methanol is hydrogenolyzed for 4 hours under 3 atmospheres of hydrogen in the presence of 0.1 g. of 5% palladium on carbon. The catalyst is removed by filtration and the filtrate concentrated to dryness under reduced pressure. Excess acid is removed by co-distillation with methanol under reduced pressure to give 0.071 g. of 3-de-O-methylfortimicin A tetrahydrochloride: $[\alpha]_D^{23} + 79.4°$ (c1.0, $CH_3OH$); IR 3410, 2930, 1639, 1595, 1483 $cm^{-1}$; PMR ($D_2O$) δ 1.81 ($C_6'$-$CH_3$, $J_{6'7}=6.5$), 3.62 ($C_4$-N-$CH_3$), 5.79 ($H_{1'}$, $J_{1',2'}=3.5$); Mass spec. M+ 391.2414, Calculated for $C_{16}H_{33}N_5O_6$ 391.2431.

EXAMPLE 7

3-De-O-methyl-4-N-sarcosylfortimicin B tetrahydrochloride

Tetra-N-benzyloxycarbonyl-3-de-O-methyl-4-N-sarcosylfortimicin B (0.125 g.) in 25 ml. 0.2 N hydrochloric acid in methanol is hydrogenolyzed for 4 hours under 3 atmospheres of hydrogen in the presence of 0.13 g. of 5% palladium on carbon. The catalyst is removed by filtration and the filtrate concentrated to dryness under reduced pressure. Excess acid is removed by co-distillation with methanol under reduced pressure to give 0.073 g. of 3-de-O-methyl-4-N-sarcosylfortimicin B tetrahydrochloride: $[\alpha]_D^{24} + 83.5$ (c 1.01, $CH_3OH$); IR 3420, 2930, 1635, 1485 $cm^{-1}$; PMR ($D_2O$) 1.8 ($C_6'$-$CH_3$, $J_{6',7}=6.5$), 3.27 (Sarcosyl-N-$CH_3$), 3.6 ($C_4$-N-$CH_3$), 5.79 ($H_{1'}$, $J_{1',2'}=3.5$); Mass Spec M+405.2614, Calculated for $C_{17}H_{35}N_5O_6$ 405.2587.

EXAMPLE 8

Tetra-N-benzyloxycarbonyl-3-de-O-methyl-4-N-(β-aminoethyl)-fortimicin B

To an ice cold stirred solution of 0.3 g. of tetra-N-benzyloxycarbonyl-3-de-O-methylfortimicin A in dry tetrahydrofuran (6 ml.) is added 1.0 ml. of a 1 M solution of diborane in tetrahydrofuran. The reaction mixture is stirred for 3 hours under a nitrogen atmosphere and then treated with an additional 1.0 ml. of the diborane solution. After stirring for an additional 2 hours under nitrogen, water is added and the solvents evaporated under reduced pressure. Purification by column chromatography on silica gel prepared and eluted with a solvent system consisting of chloroform-methanol-concentrated ammonium hydroxide (23.4:1.4:0.1 v/v/v) gave pure tetra-N-benzyloxycarbonyl-3-de-O-methyl-4-N-(β-aminoethyl)fortimicin B.

EXAMPLE 9

3-De-O-methyl-4-N-(β-aminoethyl)fortimicin B tetrahydrochloride

Tetra-N-benzyloxycarbonyl-3-de-O-methyl-4-N-(β-aminoethyl)-fortimicin B (0.10 g.) in 25 ml. of 0.2 N hydrochloric acid in methanol is hydrogenolyzed for 4 hours under 3 atmospheres of hydrogen in the presence of 0.11 g. of 5% palladium on carbon. The catalyst is removed by filtration and the filtrate concentrated to dryness under reduced pressure. Excess acid is removed by co-evaporation with methanol under reduced pressure to give 3-de-O-methyl-4-N-(β-aminoethyl)fortimicin B tetrahydrochloride.

EXAMPLE 10

3-De-O-methyl-4-N-(β-aminoethyl)fortimicin B

To a solution of 1.0 g. of 4-N-(β-aminoethyl)fortimicin B in 25 ml. of freshly distilled ethylamine is added 20 ml. of ethylamine containing 0.430 g. of lithium wire freshly cut into small pieces. The dark blue reaction mixture is stirred under reflux for 2–16 hours, then methanol is cautiously added to consume the excess lithium. The solvent is evaporated under reduced pressure and the residue chromatographed on silica gel prepared and eluted with the lower phase of a mixture of chloroform-methanol-concentrated ammonium hydroxide (1:1:1 v/v/v). Fractions containing the desired product are collected and rechromatographed on a column of a weakly acidic, carboxylic (polymethacrylic) type, cation exchange resin, Bio Rex 70.100-200 mesh, sold by Bio-Rad Laboratories (ammonia form). Elution with a gradient of water to 1 N $NH_4OH$ gives fractions containing pure 3-de-O-methyl-4-N-(β-aminoethyl)fortimicin B.

EXAMPLE 11

3-De-O-methyl-2'-N-Glycylfortimicin B

An aqueous solution of 10.0 g of 3-de-O-methyl fortimicin A disulfate is passed through a column of an anion exchange resin, quaternary ammonium styrene type, e.g., Bio-Rad Laboratories, AG ® 2-X8, 100–200 mesh, hydroxyl form, sufficient to remove the sulfate ion. The basic elutes are collected and diluted with water to a 1% solution based on starting 3-de-O-methyl fortimicin A disulfate. After standing at 37° C. for 20 days the water is evaporated under reduced pressure to leave an oil. A 2.07 g portion of the oil is chromatographed on a column (2.2 × 52 cm) of a cation exchange resin, carboxylic type, e.g., Bio-Rad Laboratories, Bio-Rex 70, 100–200 mesh, and eluted with 0.1 N ammonium hydroxide. Elutes containing only the desired product are collected, evaporated to small volume under reduced pressure and lyophilized to give the desired product as a solid.

EXAMPLE 12

3-De-O-methyl-2'-N-(N-benzyloxycarbonylglycyl)-1,6'-di-N-benzyloxycarbonylfortimicin B A stirred solution of 0.333 g. of 3-de-O-methyl-2'-N-glycylfortimicin B in 4.5 ml of water and 9.0 ml of methanol, cooled to 4° C. in an ice bath, is treated with 0.666 g of N-(benzyloxycarbonyloxy)succinimide. Stirring is continued at 4° C. for 3 hours and then at room temperature for 20 hours. The resulting solution is concentrated under reduced pressure to an oil. The oil is shaken with a mixture of 150 ml of chloroform and 75 ml of water. The chloroform layer is separated and washed with 75 ml of water. The aqueous portions are washed in series with two 75 ml portions of chloroform. The chloroform solutions are combined and dried over anhydrous magnesium sulfate. Evaporation of the chloroform under reduced pressure leaves 0.596 g of product. The product is chromatographed on a column (1.8×48 cm) of silica gel prepared and eluted with a solvent system consisting of chloroform methanol-ammonium hydroxide (23.4:1.4:0.1 v/v) to yield the desired product.

EXAMPLE 13

3-De-O-methyl-tetra-N-benzyloxycarbonyl-2'-N-glycylfortimicin A

To a stirred solution of 0.234 g. of 3-de-O-methyl-2'-N-(N-benzyloxycarbonylglycyl)-1,6'-N,N'-di-N-benzyloxycarbonylfortimicin B, 0.105 g. of N-benzyloxycarbonylglycine and 0.939 g. of 1-hydroxybenzotriazole monohydrate in 2.0 ml tetrahydrofuran is added 0.087 g. of N,N-dicyclohexylcarbodiimide in 2.0 ml of tetrahydrofuran. Stirring is continued for 20 hours at room temperature. Insoluble dicyclohexylurea is removed by filtration and the filtrate is concentrated to dryness under reduced pressure leaving a residue which is chromatographed on a column (1.8×42 cm) of silica gel eluted with a solvent system consisting of benzenemethanol-95% ethanol-ammonium hydroxide (23.5:1.4:2.0:0.2 v/v/v/v) to give the desired product.

EXAMPLE 14

3-De-O-methyl-2'-N-glycylfortimicin A tetrahydrochloride

A solution of 0.235 g. of 3-de-O-methyl-tetra-N-benzyloxycarbonyl-2'-N-glycylfortimicin A in 40 ml of 0.2 N hydrochloric acid in methanol is hydrogenolyzed for 4 hours under 3 atmospheres of hydrogen in the presence of 0.235 g of 5% palladium on carbon. The catalyst is removed by filtration through a celite mat. The filtrate is concentrated to dryness and excess hydrochloric acid is removed by repeated co-distillation with methanol under reduced pressure to give the desired 3-de-O-methyl-2'-N-glycylfortimicin A tetrahydrochloride.

EXAMPLE 15

3-De-O-methyl-1,2',6'-tri-N-benzyloxycarbonyl fortimicin B

To a stirred solution of 2.0 g. of 3-de-O-methylfortimicin B, 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromotographed on silica gel. Elution with a solvent system composed of chloroform-methanol-ammonium hydroxide (23.4:1.4:0.1 v/v/v) yields the desired product.

EXAMPLE 16

3'De-O-methyl-1,2',6'-tri-N-benzyloxycarbonyl-4-N-acetylfortimicin B

To a stirred solution of 3.22 g. of 3-de-O-methyl-1,2',6'-tri-N-benzyloxycarbonylfortimicin B in 225 ml of methanol, cooled in an ice bath, is added 16 ml of acetic anhydride over a 15 minute period. Stirring is continued at 0° for 2 hours and then at room temperature for 2 hours. The methanol is evaporated under reduced pressure and residual acetic anhydride and acetic acid are removed by co-distillation with benzene and methanol to leave the final product.

EXAMPLE 17

3-De-O-methyl-4' N-Acetylfortimicin B Trichloride

A solution of 1.0274 g. of 3-de-O-methyl-tri-N-benzyloxycarbonyl-4-N-acetylfortimicin B in 180 ml of 0.2 N hydrochloric acid in methanol is hydrogenolyzed over 1.2 g of 5% palladium on carbon for 4 hours. The catalyst is removed by filtration through a celite mat. The filtrate is concentrated to dryness under reduced pressure and excess hydrochloric acid is removed by repeated co-distillation with methanol under reduced pressure to give the desired product.

EXAMPLE 18

3-De-O-methyl-2'-N-acetylfortimicin B

An aqueous solution of 0.840 g. of 3-de-O-methyl-4-N-acetylfortimicin B trihydrochloride is passed through a column (1.1×19 cm) of an anion exchange resin, quaternary ammonium styrene type, e.g., Bio-Rad Laboratories' AG® 2-X8, 50–100 mesh, (hydroxyl form), sufficient to remove the chloride ion. The basic elutes are collected and diluted to 84 ml with water. After standing at room temperature for 20 days the solution is evaporated under reduced pressure to a small volume and chromatographed on a column of a cation exchange resin, carboxylic type, e.g., Bio-Rad Laboratories' Bio-Rex 70, 100–200 mesh, ammonium form. Elution with a gradient of water to 1 N ammonium hydroxide gives fractions containing only 3-de-O-methyl-2'-N-acetylfortimicin B. These fractions are concentrated to dryness under reduced pressure to give the desired product.

EXAMPLE 19

3-De-O-methyl-1,6'-di-N-benzyloxycarbonyl-2'-N-acetylfortimicin B

A stirred solution of 0.290 g. of 3-de-O-methyl-2'-N-acetylfortimicin B in 4.5 ml of water and 9.0 ml of methanol, cooled to 0° C. in an ice bath, is treated with 0.388 g of N-(benzyloxycarbonyloxy)succinimide. Stirring is continued at 0° C. for 3 hours and then at room temperature for 22 hours. The solution is concentrated under reduced pressure to an oil which is shaken with a mixture of 100 ml of chloroform and 75 ml of water. The chloroform layer is separated and the aqueous portion is shaken with an additional 100 ml of chloroform. The combined chloroform solutions are washed two times with water and dried over anhydrous magnesium sulfate. Evaporation of the chloroform under reduced pressure leaves a solid which is chromatographed on a column (2.0×43 cm) of silica gel prepared and eluted with a solvent system consisting of chloroform, methanol, concentrated ammonium hydroxide (23.4:1.4:01 v/v/v) to give 3-de-O-methyl-1,6'-di-N-dibenzyloxycarbonyl-2'-N-acetylfortimicin B.

EXAMPLE 20

3-De-O-methyl-tri-N-benzyloxycarbonyl-2'-N-acetylfortimicin A

To a stirred solution of 0.150 g. of 3-de-O-methyl-1,6'-di-N-benzyloxycarbonyl-2'-N-acetylfortimicin B, 0.065 g of N-benzyloxycarbonylglycine and 0.074 g of 1-hydroxybenzotriazole monohydrate in 2.0 ml of tetrahydrofuran is added a solution of 0.069 g of N,N'-dicyclohexylcarbodiimide in 2.0 ml of tetrahydrofuran. Stirring is continued at room temperature for 23 hours. The precipitated N,N'-dicyclohexylurea is removed by filtration. The filtrate is evaporated under reduced pressure to leave a residue which is chromatographed on a column of silica gel, prepared and eluted with a solvent system consisting of benzene-methanol-95% ethanol-conc. ammonium hydroxide (23.5:1.4:2.0:0.2 v/v). Fractions containing the desired product were taken to dryness under reduced pressure leaving 3-de-O-methyl-tri-N-benzyloxycarbonyl-2'-N-acetylfortimicin A.

EXAMPLE 21

3-De-O-methyl-2'-N-acetylfortimicin A Trihydrochloride

A solution of 0.178 g. of 3-de-O-methyl-tri-N-benzyloxycarbonyl-2'-N-acetylfortimicin A in 30 ml of 0.2 N hydrochloric acid in methanol is hydrogenolyzed for 4 hours under 3 atmospheres of hydrogen in the presence of 0.178 - of 5% palladium on carbon. The catalyst is removed by filtration through a celite mat. The filtrate is concentrated to a small volumn and treated with activated carbon, e.g., Darco®G-60, sold by Atlas Chemical Industries, Inc. The carbon is removed by filtration through a celite mat. The filtrate is concentrated to dryness and excess hydrochloric acid is removed by repeated co-distillation with methanol under reduced pressure to give the desired product.

EXAMPLE 22

3-De-O-methyl-2'-N-($\beta$-aminoethyl)fortimicin B

A stirring solution of 2.0 g. of 3-de-O-methyl-2'-N-glycylfortimicin B in 80 ml of tetrahydrofuran is treated with 1.22 g. of lithium aluminum hydride. The stirring reaction mixture is refluxed for 20 hours and then the excess lithium aluminum hydride is consumed by the careful addition of water. The insoluble material is sedimented by centrifugation. The pellet is suspended in 50 ml. of water and centrifuged. The combined supernatants are taken to dryness under reduced presure. The resulting solid is chromatographed on a column (2.0×40 cm) of cation exchange resin, carboxylic type, e.g., Bio-Rad Laboratories' Bio-Rex 70, 100–200 mesh, (ammoni form), and eluted with a gradient of water to 1 N ammonium hydroxide. Fractions containing the desired product are concentrated to a small volume and lyophilized to give 3-de-O-methyl-2'-N-($\beta$-aminoethyl)fortimicin B.

EXAMPLE 23

3-De-O-methyl-1,6'-di-N-benzyloxycarbonyl-2'-N-[N-benzyloxycarbonyl)$\beta$-aminoethyl)]fortimicin B A stirred solution of 0.824 g. of 3-de-O-methyl-2'-N-($\beta$-aminoethyl)fortimicin B in 12.4 ml of water and 24.8 ml of methanol cooled to 4° in an ice bath, is treated with 1.83 g of N-(benzyloxycarbonyl)succinimide. Stirring is continued at 4° for 3 hours and then at room temperature for 22 hours. The reaction mixture is concentrated to an oil under reduced pressure and then it is shaken with a mixture of 150 ml of chloroform and 75 ml of water. The chloroform layer is separated and washed with 75 ml of water. The aqueous portions are then washed in series with two 80 ml portions of chloroform. The combined chloroform solution is dried over anhydrous magnesium sulfate and concentrated to dryness under reduced pressure to give a residue which is chromatographed on a column (2.2×65 cm) of silica gel prepared and eluted with a solvent system consisting of benzene-methanol-95% ethanol-ammonium hydroxide (23.5:1.4:2.0:0.2 v/v/v/v) to give 3-de-O-methyl-1,6'-di-B-benzyloxycarbonyl-2'-N-[N-benzyloxycarbonyl)$\beta$-aminoethyl)fortimicin B.

EXAMPLE 24

3-De-O-methyl-1,6'-di-N-benzyloxycarbonyl-2'-N-[N-benzyloxycarbonyl($\beta$-aminoethyl)]-4-N-(N-benzyloxycarbonylglycyl)fortimicin B A stirred solution of 0.503 g. of 3-de-O-methyl-1,6-di-N-benzyloxycarbonyl-2'-N-[N-benzyloxycarbonyl($\beta$-aminoethyl)]-fortimicin B in 3.4 ml of tetrahydrofuran is treated with 0.223 g of the N-hydroxysuccinimide ester of N-benzyloxycarbonylglycine. After stirring for 20 hours at room temperature the tetrahydrofuran is evaporated under reduced pressure to leave 0.714 g of colorless solid. The solid is chromatographed on a column (1.5×74 cm) of silica gel eluted with a solvent system consisting of benzene-methanol-95% ethanol-ammonium hydroxide (23.5:1.4:2.0:0.2 v/v/v/v) to give the desired product.

EXAMPLE 25

3-De-O-methyl-2'-N-($\beta$-aminoethyl)fortimicin A pentahydrochloride

A solution of 0.426 g. of 3-de-O-methyl-1,6'-di-N-benzyloxycarbonyl-2'-N-[N-benzyloxycarbonyl($\beta$-aminoethyl)]-4-N-(N-benzyloxycarbonylglycylfortimicin B in 70 ml of 0.2 N methanolic hydrochloric acid is hydrogenolyzed over 0.40 g of 5% palladium on carbon for 4 hours. The catalyst, collected by filtration through a celite mat, is washed with several small portions of methanol. The filterate is evaporated to dryness under reduced pressure. Excess hydrochloric acid is removed by repeated co-distillation with methanol under reduced pressure to give the desired product.

The compounds of this invention are active as systemic antibiotics when injected by parenteral routes of administration, i.e., by the intramuscular, intravenous, intraperitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 1 to 100 mg/kg of body weight daily are administered to a mammalian patient suffering from an injection caused by susceptible organism.

We claim:

1. A compound of the formula:

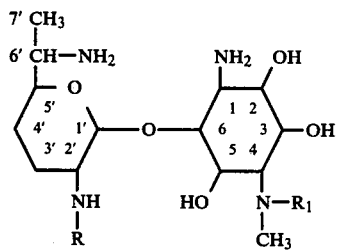

wherein; R is acyl, aminoacyl, N-monoloweralkylaminoacyl, N,N-diloweralylaminoacyl, hydroxy-substituted aminoacyl, a chiral amino acid residue, loweralkyl, aminoloweralkyl, hydroxyacyl, an alkyl, N-loweralkylaminoloweralkyl, N,N-diloweralkylaminoloweralkyl, aminohydroxyloweralkyl, N-loweralkylaminohydroxyloweralkyl, or N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, an amino acid residue, hydroxyacyl, loweralkyl, aminoloweralkyl, hydroxyloweralkyl, N-loweralkylaminoloweralkyl, N,N-diloweralkylminoloweralkyl, aminohydroxyloweralkyl, N-loweralkylaminohydroxyloweralkyl, N,N-diloweralkylaminohydroxyloweralkyl or hydrogen wherein acyl is

Y being loweralkyl; and the pharmaceutically acceptable salts thereof.

2. A compound of claim 1 wherein $R_1$ is hydrogen.

3. 3-De-O-methyl-2'-N-glycylfortimicin B or a pharmaceutically acceptable salt thereof.

4. 3-De-O-methyl-2'-N-acetylfortimicin B, or a pharmaceutically acceptable salt thereof.

5. A compound of the formula

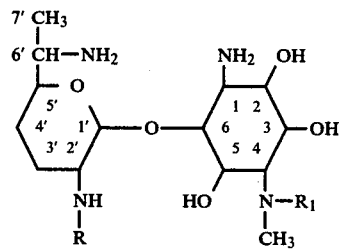

wherein both R and $R_1$ are an amino acid residue.

6. A compound of claim 5: 3-de-O-methyl-2'-N-glyclfortimicin A or a pharmaceutically acceptable salt thereof.

7. A compound of claim 1 wherein R is aminoloweralkyl.

8. 3-De-O-methyl-2'-N-($\beta$-aminoethylfortimicin B or a pharmaceutically acceptable salt thereof.

9. 3-De-O-methyl-2'-N-($\beta$-aminoethyl)fortimicin A or a pharmaceutically acceptable salt thereof.

10. A pharmaceutical composition comprising a compound of claim 1 and a pharmaceutically acceptable carrier or diluent.

* * * * *